US009877652B2

(12) United States Patent
Nakagawa

(10) Patent No.: US 9,877,652 B2
(45) Date of Patent: Jan. 30, 2018

(54) MEDICAL MEASUREMENT DEVICE AND MEASUREMENT SYSTEM

(71) Applicant: ARKRAY, INC., Kyoto-shi, Kyoto (JP)

(72) Inventor: Takashi Nakagawa, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 390 days.

(21) Appl. No.: 14/181,349

(22) Filed: Feb. 14, 2014

(65) Prior Publication Data

US 2014/0232554 A1    Aug. 21, 2014

(30) Foreign Application Priority Data

Feb. 18, 2013  (JP) .................................. 2013-028907
Jan. 27, 2014  (JP) .................................. 2014-012317

(51) Int. Cl.
*G08C 19/12*    (2006.01)
*A61B 5/00*     (2006.01)
(Continued)

(52) U.S. Cl.
CPC .......... *A61B 5/0015* (2013.01); *A61B 5/0004* (2013.01); *G08C 17/02* (2013.01);
(Continued)

(58) Field of Classification Search
CPC ... A61B 5/0002; A61B 5/0024; A61B 5/0004; A61B 5/0015; A61B 5/002;
(Continued)

(56) References Cited

U.S. PATENT DOCUMENTS 6,246,966 B1 *  6/2001  Perry ..................... C12Q 1/006
                                                600/368
6,300,880 B1 * 10/2001  Sitnik .................... H04L 29/06
                                                235/375
(Continued)

FOREIGN PATENT DOCUMENTS

EP    2001188 A1    12/2008
EP    2517620 A1    10/2012
(Continued)

OTHER PUBLICATIONS

The first Office Action issued by the Chinese Patent Office dated Jun. 30, 2015, which corresponds to Chinese Patent Application No. 201410051095.X and is related to U.S. Appl. No. 14/181,349; with English language partial translation.

(Continued)

*Primary Examiner* — Omeed Alizada
(74) *Attorney, Agent, or Firm* — Studebaker & Brackett PC

(57) ABSTRACT

A measurement device includes: a measurement portion that acquires measurement data; a setting portion that specifies an external device as a transmission destination of the measurement data based on a signal transmitted from the external device, and allows communication with the external device without receiving input of authentication information; and a transmission and reception portion that transmits measurement data to the external device. The setting portion causes the transmission and reception portion to transmit identification information of the measurement device to the external device, and further to transmit confirmation information thereto in addition to the identification information. The confirmation information is used by the external device to decide whether or not the external device can handle the (Continued)

measurement data transmitted from the measurement device.

14 Claims, 9 Drawing Sheets

(51) Int. Cl.
  *G08C 17/02* (2006.01)
  *G08C 23/04* (2006.01)
  *A61B 5/145* (2006.01)
(52) U.S. Cl.
  CPC .............. *G08C 23/04* (2013.01); *A61B 5/002* (2013.01); *A61B 5/14532* (2013.01)
(58) Field of Classification Search
  CPC . A61B 5/14532; G06F 19/3418; G08C 17/02; G08C 23/04
  USPC .................................................... 340/539.12
  See application file for complete search history.

(56) References Cited

U.S. PATENT DOCUMENTS

| | | | | |
|---|---|---|---|---|
| 7,333,025 | B2* | 2/2008 | Oosugi | H04B 1/202 340/12.28 |
| 2008/0022281 | A1* | 1/2008 | Dubhashi | G06F 9/547 718/102 |
| 2009/0033513 | A1* | 2/2009 | Salsbury | H04W 24/00 340/4.2 |
| 2009/0299289 | A1* | 12/2009 | Kamen | A61M 5/1413 604/151 |
| 2010/0115279 | A1* | 5/2010 | Frikart | G06F 19/3406 713/171 |
| 2011/0050401 | A1* | 3/2011 | Shimazaki | G06Q 30/02 340/10.42 |
| 2011/0221590 | A1* | 9/2011 | Baker | A61B 5/0002 340/539.12 |
| 2012/0274443 | A1* | 11/2012 | Kai | A61B 5/0002 340/5.61 |

FOREIGN PATENT DOCUMENTS

| | | |
|---|---|---|
| JP | 2000-029972 A | 1/2000 |
| JP | 2002-291069 A | 10/2002 |
| JP | 2003-144394 A | 5/2003 |
| JP | 2008-035426 A | 2/2008 |
| JP | 2009-181593 A | 8/2009 |
| JP | 2012-237748 A | 12/2012 |
| WO | 02/056536 A1 | 7/2002 |

OTHER PUBLICATIONS

The extended European search report dated Apr. 16, 2014, which corresponds to European Patent Application No. 14155281.0-1955 and is related to U.S. Appl. No. 14/181,349.
An Office Action; "Notice of Reasons for Rejection," issued by the Japanese Patent Office dated Feb. 17, 2015, which corresponds to Japanese Patent Application No. 2014-012317 and is related to U.S. Appl. No. 14/181,349.
Communication pursuant to Article 94(3) EPC issued by the European Patent Office dated Jul. 5, 2017, which rresponds to European Patent Application No. 14 155 281.0-1657 and is related to U.S. Appl. No. 14/181,349.

\* cited by examiner

MEDICAL MEASUREMENT DEVICE AND MEASUREMENT SYSTEM

CROSS REFERENCE TO RELATED APPLICATIONS

This application claims benefit of priority to Japanese Patent Application No. 2013-028907, filed Feb. 18, 2013, and to Japanese Patent Application No. 2014-012317, filed Jan. 27, 2014, the entire content of each of which is incorporated herein by reference.

TECHNICAL FIELD

The present invention relates to a technique for acquiring information about a subject body and processing the information.

BACKGROUND

For example, most of medical measurement devices such as a portable blood glucose meter have a function of transmitting measurement data of a subject body obtained by measurement to another device. For example, JP 2000-29972 A and JP 2009-181593 A disclose a system of transmitting data of blood glucose levels recorded in a clinical analysis device to a computer system, together with an identification password. Further, JP 2003-144394 A discloses a case of transmitting control log information to a server simultaneously with biological information from a patient terminal and analyzing the information in the server.

Recently, along with the spread of communication devices, setting of data communication between a medical measurement device and a user's communication device (e.g., smartphone, tablet terminal, etc.) is increasing. For example, a pairing operation sometimes is required that allows wireless communication between a measurement device and an external device. At this time, a setting operation of a measurement device by a user is demanded to be as simple as possible. However, when the setting operation for communication with an external device is facilitated, unauthorized access from the outside may increase and erroneous communication with another device may be established. The above-described conventional techniques do not disclose measures for solving such problems in the communication setting between a measurement device and an external device.

Conventionally, when establishing the communication between a measurement device and an external device, at least one of the measurement device and the external device requires a user to input authentication information for authenticating the other device. The authentication information is used at the time of establishing communication between devices so as to confirm before establishing the communication that the other device is a communication partner. For example, in order to facilitate an operation at the time of establishing communication, if both of the measurement device and the external device do not require input of authentication information, communication may be established between erroneous devices. Particularly in a medical field, it is assumed that a plurality of users perform communication setting between their own measurement devices and external devices simultaneously in the same place. To cope with this situation, a communication setting operation of a measurement device with respect to an external device should be facilitated, while avoiding establishment of communication with an erroneous external device. The present application discloses a technique of preventing communication from being set erroneously while simplifying a communication setting operation between a medical measurement device and an external device.

SUMMARY

A medical measurement device disclosed by the present application is a medical measurement device that acquires information about a subject body, including: a measurement portion that acquires measurement data obtained by measurement; a setting portion that specifies an external device as a transmission destination of the measurement data based on a signal transmitted from the external device, and records information of the specified external device, thereby allowing communication with the external device without receiving input of authentication information; and a transmission and reception portion that transmits the measurement data to the external device specified by the setting portion and receives data from the external device. The setting portion causes the transmission and reception portion to transmit identification information of the measurement device for enabling mutual communication with respect to the external device as a transmission source of the received signal, and further to transmit or receive confirmation information that is used for a decision of whether or not the measurement data transmitted from the measurement device can be handled between the measurement device and the external device.

According to the disclosure of the present application, it is possible to prevent communication from being set erroneously while simplifying a communication setting operation between a medical measurement device and an external device.

DETAILED DESCRIPTION

Embodiment 1

Exemplary Configuration of System

Figure 1:
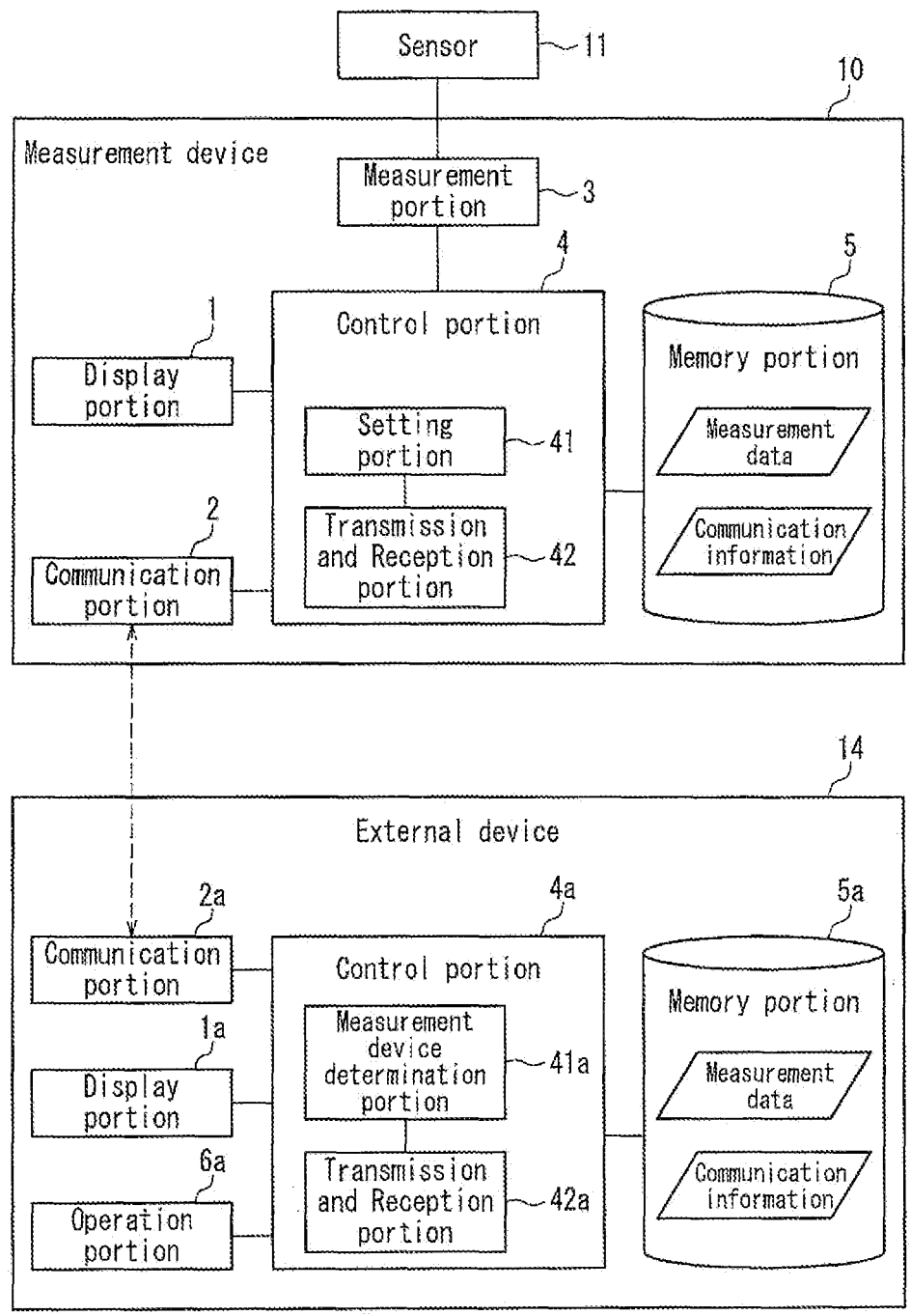
FIG. 1 is a functional block diagram showing an exemplary configuration of a measurement system according to Embodiment 1 of the present invention.

FIG. 1 is a functional block diagram showing an exemplary configuration of a measurement system according to Embodiment 1 of the present invention. The measurement system shown in FIG. 1 includes a measurement device 10 and an external device 14. The measurement device 10 acquires information about a subject body obtained by measurement, and records the information. The external device 14 receives measurement data from the measurement device 10, and processes the data.

As one example, the present embodiment describes a case where the measurement device 10 is a portable blood glucose meter (glucometer) used for measuring a user's own glucose level, and the external device 14 is a general-purpose computer such as a personal computer, a smartphone and a tablet terminal of a user. However, the measurement device 10 and the external device 14 are not limited to particular devices.

Exemplary Configuration of Measurement Device 10

In the example shown in FIG. 1, the measurement device 10 is provided with a display portion 1, a communication portion 2, a measurement portion 3, a control portion 4, and a memory portion 5. The measurement portion 3 acquires measurement data obtained by measurement. For example, the measurement portion 3 provides the control portion 4 with measurement values based on information obtained via a sensor 11. The control portion 4 includes a setting portion 41 and a transmission and reception portion 42. The setting portion 41 specifies an external device as a transmission destination of measurement data based on a signal transmitted from the external device, and records information of the specified external device, thereby allowing communication with the external device. At this time, the setting portion 41 brings the measurement device 10 into a state communicable with the external device without receiving input of authentication information. The transmission and reception portion 42 includes a transmission portion that transmits measurement data to the external device specified by the setting portion 41. Further, the transmission and reception portion 42 can receive signals and the like from the external device. Other than this explanation, the transmission portion and the reception portion may be independent from each other.

The setting portion 41 causes the transmission and reception portion 42 to transmit identification information of the measurement device for enabling mutual communication, with respect to the external device as a transmission source of the received signal. Further, the setting portion 41 causes the transmission and reception portion 42 to transmit confirmation information with respect to the external device in addition to the identification information at or after the transmission of the identification information. The confirmation information is used by the external device to decide whether or not the external device can handle the measurement data transmitted from the measurement device 10.

In the above-described configuration, the measurement device 10 receives a signal from the external device, records information of the external device, and transmits identification information of the measurement device to the external device, thereby simplifying a user's operation when establishing communication with the external device. For example, the above-described configuration allows bidirectional communication without reception of authentication information from a user both in the external device and the measurement device. Further, the measurement device 10 transmits confirmation information to the external device at or after the establishment of communication with the external device as a transmission destination of measurement data. Thus, the external device can decide using the confirmation information whether or not erroneous communication is set between the external device and the measurement device 10. In other words, the transmission of confirmation information from the measurement device 10 to the external device makes it possible to detect an erroneous, not-intended communication setting.

The confirmation information may include information specific to the measurement device 10, for example. Examples of the confirmation information include a product serial number of the measurement device 10, a user's telephone number, a preset password, etc. The confirmation information transmitted from the measurement device 10 is, for example, compared with authentication information input from a user in the external device. Thus, the propriety of the established communication can be judged based on the comparison result.

The setting portion 41 can be configured to cause the transmission and reception portion 42 to transmit confirmation information to the external device, after specifying the external device as a transmission destination of measurement data and allowing communication with the external device. In this manner, by establishing communication with the external device and thereafter transmitting confirmation information to the external device, the measurement device 10 can establish communication with a simple operation and thereafter judge the propriety of the established communication. For example, the setting portion 41 also may be configured to cause the transmission and reception portion 42 to transmit confirmation information to the external device together with measurement data, after specifying the external device as a transmission destination of measurement data and establishing communication with the external device. Thus, the external device can judge whether or not the transmitted measurement data is data from the measurement device under legitimately established communication.

The setting portion 41 can cause the display portion 1 of the measurement device 10 to display confirmation information, thereby allowing a user to know confirmation information of the measurement device 10. When the measurement device 10 and the external device in communication are placed close to each other, a user can check confirmation information displayed on the measurement device 10 and input it to the external device. The external device can decide the propriety of the established communication based on whether or not the confirmation information input from a user matches the confirmation information transmitted from the measurement device 10. Thus, it is possible to confirm that the communication established between the external device and the measurement device 10 is communication intended by a user. In this case, the setting portion 41 can cause the display portion 1 to display confirmation information at the timing of transmitting confirmation information.

The setting portion 41 can cause the transmission and reception portion 42 to transmit confirmation information to the external device in association with measurement data to be transmitted by the transmission and reception portion 42.

The confirmation information can be information to be used by the external device to decide the usability of measurement data in the external device. Thus, on the measurement device 10 side, it is possible to easily control the usability of measurement data in the external device. For example, the setting portion 41 can generate, as confirmation information, a confirmation code and a control instruction that allows expansion of data by the confirmation code, and associate the information with transmission data to be transmitted.

The setting portion 41 can cancel the state communicable with the external device when receiving a notification from the external device that the external device has judged the measurement data as not handleable based on the confirmation information. Thereby, it is possible to cancel the erroneously established communication setting with the external device. For example, the external device can judge whether the confirmation information transmitted from the measurement device 10 matches the confirmation information input from a user, and cause the transmission and reception portion 42 to notify the measurement device 10 of the result. If the measurement device 10 receives the notification from the external device that they do not match each other, the setting portion 41 can cancel the state communicable with the external device. Examples of the cancellation processing include processing in the measurement device 10 of deleting information of the external device registered as a transmission destination of measurement data, and the like.

Exemplary Configuration of External Device 14

In the example shown in FIG. 1, the external device 14 is provided with a communication portion 2a, a display portion 1a, an operation portion 6a, a control portion 4a, and a memory portion 5a. The control portion 4a includes a measurement device determination portion 41a, and a transmission and reception portion 42a. The measurement device determination portion 41a specifies a measurement device as a transmission source of measurement data based on a signal from the measurement device, and allows communication with the measurement device. The transmission and reception portion 42a includes a reception portion that receives measurement data from the measurement device specified by the measurement device determination portion 41a. Further, the transmission and reception portion 42a can transmit signals and the like to the measurement device. Other than this explanation, the transmission portion and the reception portion may be independent from each other.

The measurement device determination portion 41a decides whether or not the external device can handle the measurement data transmitted from the measurement device based on confirmation information transmitted from the measurement device. Thereby, it is possible to establish communication between the external device 14 and the measurement device 10 by an easy operation, while avoiding erroneous establishment of communication.

In the present example, the communication portion 2 of the measurement device 10 and the communication portion 2a of the external device 14 are communication modules that allow wireless communication with an external device. The transmission form by the communication portion 2 is not particularly limited. The communication portion 2 can adopt a near field wireless communication technology such as Bluetooth (registered trademark), RFID, Zigbee (registered trademark), wireless LAN and UWB, or an infrared communication technology. Through the communication portion 2, the setting portion 41 can receive signals from the external device 14 and transmit confirmation information to the external device 14, and the transmission and reception portion 42 can transmit measurement data to the external device.

The display portion 1 of the measurement device 10 and the display portion 1a of the external device 14 are image display means, and can be composed of a liquid crystal display, for example. Note here that an information output means with respect to a user is not limited to the configurations of the display portions 1 and 1a. For example, the information output means may either display images on an external display connected to the measurement device 10 or the external device 14, or output sound. The operation portion 6a is an information input means to be operated by a user, and can include an input device such as a dial key and a direction key. Alternatively, the display portion and the operation portion can be formed integrally as a touch panel (display panel with touch sensor).

The measurement portion 3 may either generate measurement values by performing measurement, or acquire measurement values from the outside. For example, the measurement portion 3 can receive voltage signals indicating measurement results from the sensor 11, subject them to AD conversion, generate measurement data indicating the measurement values, and supply the data to the control portion 4. Alternatively, the measurement portion 3 may receive measurement values from an external device such as the sensor 11, and pass them to the control portion 4.

Note here that a subject to be measured by the measurement portion 3 is not particularly limited. In other words, the measurement portion 3 includes any kind of configuration having a function of generating or acquiring measurement values that can be recorded in association with measurement times. As one example, the measurement portion 3 generates measurement values based on signals or data obtained from the sensor 11 that is attachable/detachable to/from the measurement device 10.

The measurement device 10 can be composed of one computer, or a plurality of computers. The setting portion 41 and the transmission and reception portion 42 of the control portion 4 can be realized by execution of a predetermined program by a processor provided in the computer. For example, a microcontroller can be incorporated in the measurement device 10. As one example, such a microcontroller can include a core processor that constitutes the measurement portion 3, which generates measurement data by subjecting voltage signals transmitted from the sensor 11 to the AD conversion, and the control portion 4.

The external device 14 also can be composed of one computer, or a plurality of computers. The measurement device determination portion 41a and the transmission and reception portion 42a of the control portion 4a can be realized by execution of a predetermined program by a processor provided in the computer.

A recording device such as a memory and a hard disk can be used as the memory portion 5 of the measurement device 10 and the memory portion 5a of the external device 14. The memory portions 5 and 5a may be housed in the measurement device 10 or the external device 14, or may be provided outside independently from the measurement device 10 or the external device 14.

The following also are included as an embodiment of the present invention: a program for causing a computer to function as the setting portion 41 and the transmission and reception portion (transmission portion) 42, or a program for causing a computer to function as the measurement device determination portion 41a and the transmission and reception portion (reception portion) 42a, and a non-transitory recording medium that records these programs. Moreover, a method for a computer to execute these programs also is included as an embodiment of the present invention.

For example, the following program also is one embodiment of the present invention:

a program for activating a computer as a measurement device, the program causing the computer to execute:

processing of acquiring measurement data obtained by measurement;

setting processing of specifying an external device as a transmission destination of the measurement data based on a signal transmitted from the external device, and recording information of the specified external device, thereby allowing communication with the external device without receiving input of authentication information; and transmission processing of transmitting the measurement data to the external device specified by the setting processing, wherein the setting processing includes:
transmitting identification information of the measurement device for enabling mutual communication with respect to the external device as a transmission source of the received signal; and
further transmitting confirmation information thereto in addition to the identification information at or after the transmission of the identification information,
wherein the confirmation information is used by the external device to decide whether or not the external device can handle the measurement data transmitted from the measurement device.

Further, the following program also is one embodiment of the present invention:

a program for activating a computer that receives measurement data from a measurement device and processes the data, the program causing the computer to execute:

measurement device determination processing of specifying a measurement device as a transmission source of the measurement data based on a signal from the measurement device, and allowing communication with the measurement device without receiving input of authentication information; and reception processing of receiving the measurement data from the specified measurement device, wherein the measurement device determination processing of the external device includes:
receiving identification information of the measurement device from the measurement device;
receiving confirmation information therefrom in addition to the identification information at or after the reception of the identification information; and
deciding whether or not the measurement data transmitted from the measurement device can be handled based on the confirmation information.

Exemplary Operation

Figure 2:
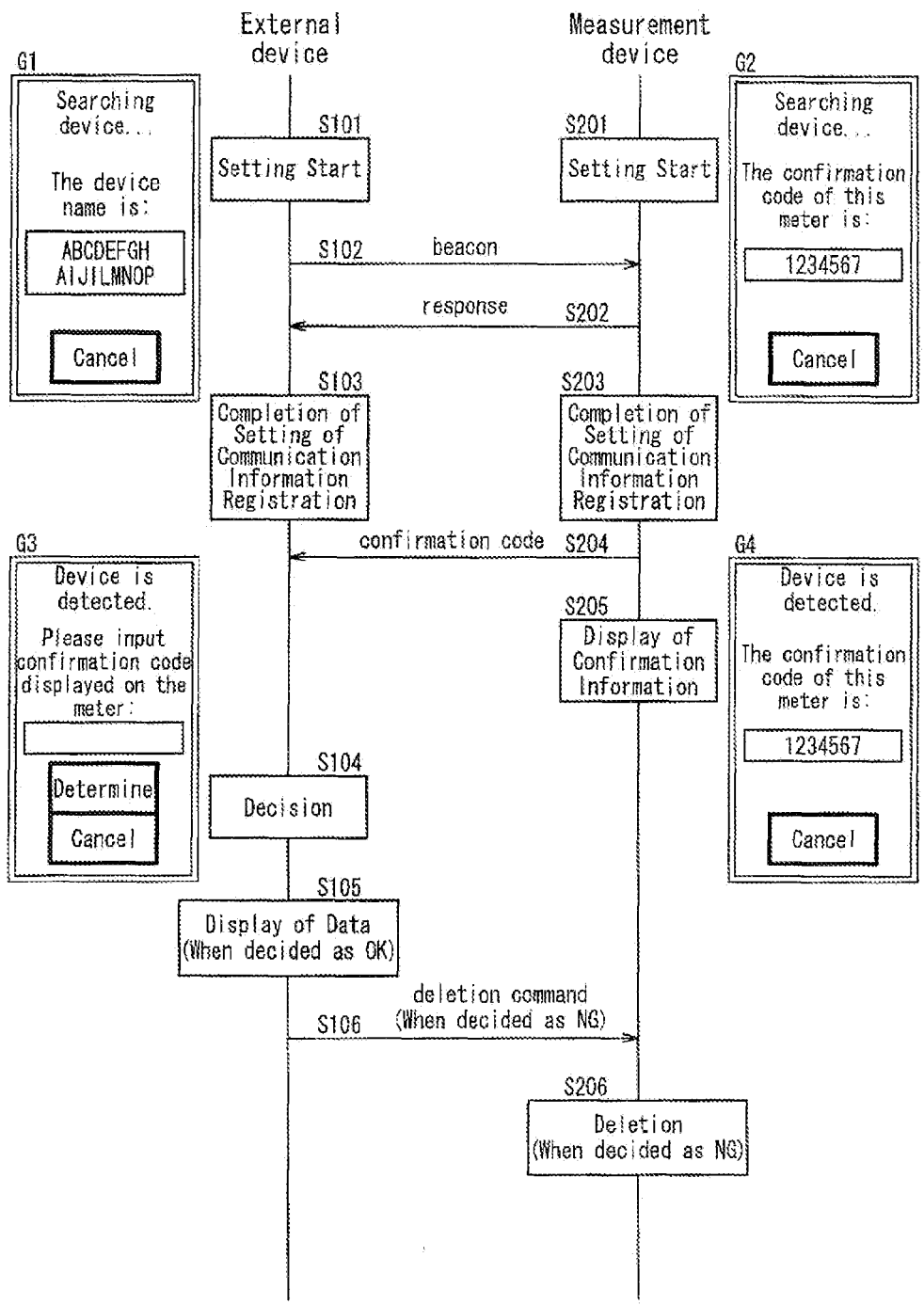
FIG. 2 is a sequence diagram showing an exemplary operation and an exemplary screen at the time of establishment of communication between a measurement device and an external device shown in FIG. 1.

FIG. 2 is a sequence diagram showing an exemplary operation and an exemplary screen at the time of establishment of communication between the measurement device 10 and the external device 14 shown in FIG. 1. The example shown in FIG. 2 is a case where the measurement device 10 and the external device 14 are paired in wireless communication based on Bluetooth (registered trademark) standards, thereby being communicable with each other. In this example, the external device 14 operates as a master, and the measurement device operates as a slave. Here, "pairing" is one exemplary processing in which the setting portion 41 of the measurement device 10 and the measurement device determination portion 41a of the external device 14 each specify a communication partner for enabling mutual communication. The pairing includes processing of authenticating a communication partner.

In the example shown in FIG. 2, first, both the external device 14 and the measurement device 10 start processing of specifying and setting a communication partner (called pairing in this example) (S101, S201). For example, a user switches the external device 14 and the measurement device 10 to a pairing mode, thereby starting pairing. G1 shown in FIG. 2 is an exemplary screen in setting start (S101) of the external device 14, and G2 is an exemplary screen in setting start (S201) of the measurement device 10.

The external device 14 transmits a beacon signal to search a peripheral device (S102). The beacon signal can contain identification information of the external device 14. The measurement device 10 that has received the beacon signal transmits a response to the external device 14 (S202). The response can contain identification information of the measurement device 10. The external device 14 that has received the response signal from the measurement device 10 records, in the memory portion 5a, information to be used for communication with the measurement device 10, such as identification information of the measurement device 10 (S103: registration of communication information). Also, the measurement device 10 records, in the memory portion 5, communication information, such as identification information of the external device 14 (S203). The communication between the measurement device 10 and the external device 14 becomes possible via S103 and S203. In other words, pairing is completed.

In the above-described example, the pairing can be completed without user's confirmation or input of identification information and authentication information (e.g., a passkey, an authentication key, a PIN, etc.) both in the external device 14 and the measurement device 10. This becomes possible by using Bluetooth (registered trademark) version 4.0, for example. In this case, before the establishment of communication between the external device 14 and the measurement device 10, the external device 14 and the measurement device 10 do not require input of authentication information so as to confirm that the other device is a connection partner.

Upon completion of pairing, the measurement device 10 transmits a confirmation code (exemplary confirmation information) to the external device 14 (S204). Further, the measurement device 10 displays the confirmation code on the display portion 1 (S205, exemplary screen G4).

In decision processing S104, the external device 14 receives input of a confirmation code from a user (exemplary screen G3), and compares the confirmation code input from the user with the confirmation code transmitted from the measurement device 10. When they match each other, the external device 14 can execute processing of data transmitted from the measurement device 10. For example, it is possible to permit an application of the external device 14 to process data (e.g., display of data (S105) etc.) transmitted from the measurement device 10.

When the confirmation code input by a user does not match the confirmation code received from the measurement device 10, or when there is no input after a certain period of time from the start of reception of input, both of the external device 14 and the measurement device 10 execute processing of invalidating the paired device. For example, the external device 14 transmits a deletion command to the measurement device 10 (S106). By deleting the communication information recorded in the memory portion 5, the measurement device 10 can invalidate the communication setting between the external device 14 and the measurement device 10 (S206). Thereby, even when erroneous pairing is established, it is possible to prevent exchange of data, leakage of personal information, etc.

Figure 3:
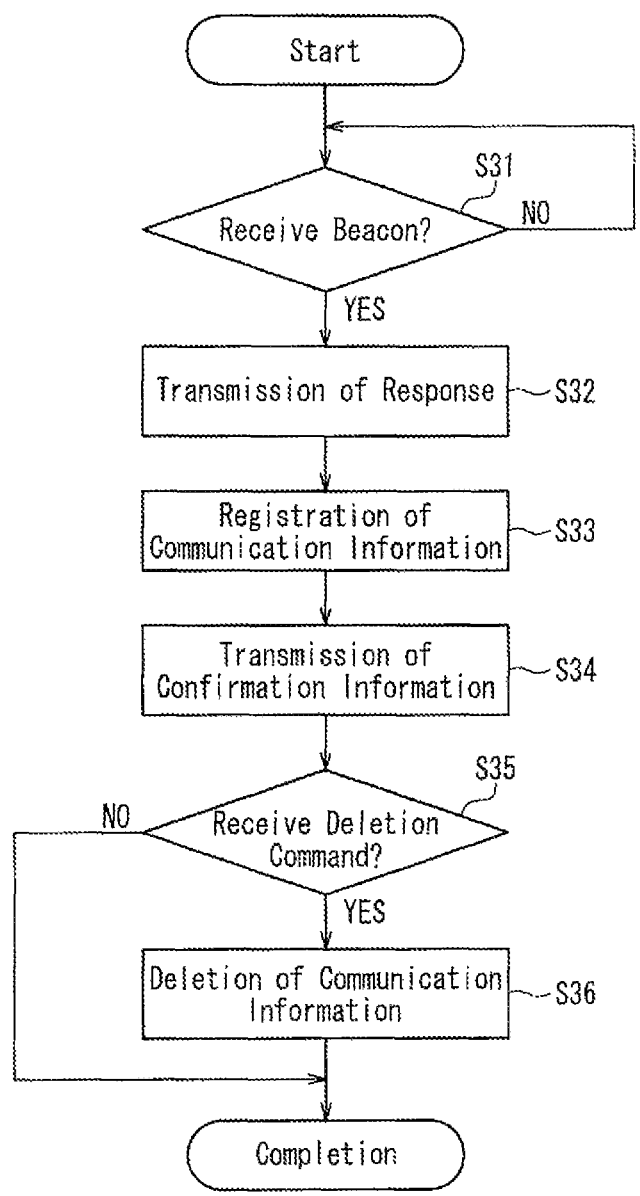
FIG. 3 is a flowchart showing exemplary setting processing by a setting portion of the measurement device shown in FIG. 1.

FIG. 3 is a flowchart showing exemplary setting processing by the setting portion 41 of the measurement device 10 shown in FIG. 1. The example shown in FIG. 3 shows exemplary processing of the measurement device 10 in the communication setting processing shown in FIG. 2. When the measurement device 10 is switched to a communication setting mode (e.g., pairing mode), the setting portion 41 waits for a beacon signal from a master device (S31). When the transmission and reception portion 42 receives a beacon signal, the setting portion 41 causes the transmission and reception portion 42 to transmit a response signal to the master device (here, the external device 14 as one example) as a transmission source of the beacon signal (S32). The response signal can contain identification information of the measurement device 10.

Upon completion of the transmission of the response signal, the setting portion 41 records, in the memory portion 5, information about the master device contained in the beacon signal received in S31 (S33), thereby allowing communication with the master device. In other words, pairing is established. In S33, communication information to be used for communication with the master device is recorded. Examples of the communication information include identification information of the master device, key information for encryption communication, etc.

The setting portion 41 causes the transmission and reception portion 42 to transmit confirmation information to the master device (S34). For example, the setting portion 41 can cause the transmission and reception portion 42 to transmit confirmation information by adding confirmation information to a header of data to be transmitted to the master device. For example, the setting portion 41 can associate confirmation information with measurement data recorded in the measurement device 10, and cause the transmission and reception portion 42 to transmit the information to the master device together with the measurement data. At that time, the confirmation information can limit the use of the measurement data in the master device. As one example, the setting portion 41 can cause the transmission and reception portion 42 to transmit, together with the confirmation information, a control instruction that allows an application of the master device to use the measurement data only when the confirmation information matches the confirmation information input from a user in the master device. Thus, on the measurement device side, it is possible to control the use of data in the master device.

When the transmission and reception portion 42 receives a deletion command from the master device in reply to the confirmation information (YES in S35), the setting portion 41 judges that pairing is established with an erroneous master device, and deletes the communication information recorded in S33 (S36), thereby canceling the pairing with the master device.

Figure 4:
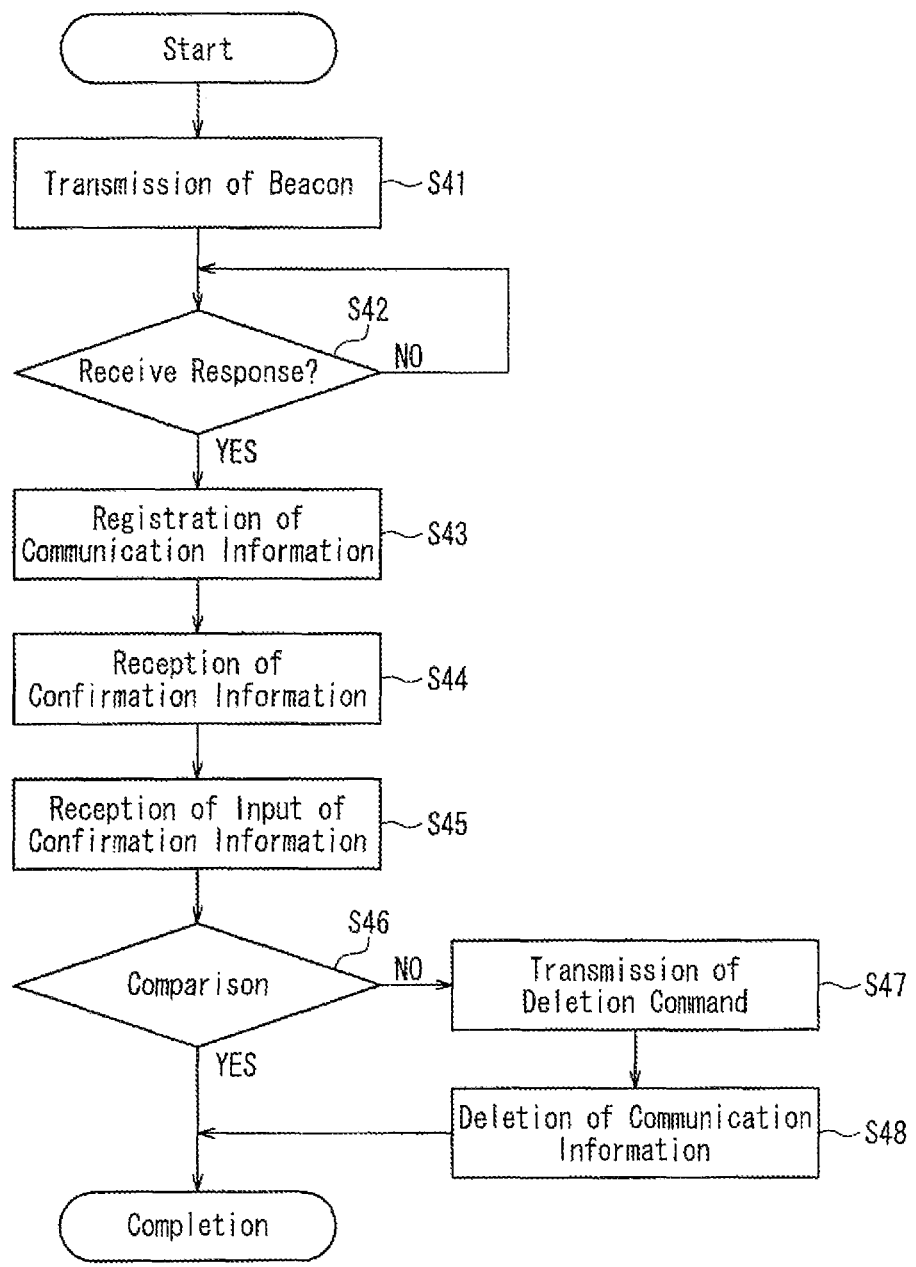
FIG. 4 is a flowchart showing exemplary setting processing by a measurement device determination portion of the external device shown in FIG. 1.

FIG. 4 is a flowchart showing exemplary setting processing by the measurement device determination portion 41a of the external device 14 shown in FIG. 1. The example shown in FIG. 4 shows exemplary processing of the external device 14 in the communication setting processing shown in FIG. 2. When the external device 14 is switched to a communication setting mode (e.g., pairing mode), the measurement device determination portion 41a causes the transmission and reception portion 42a to transmit a beacon signal to search a peripheral slave device (S41).

When the transmission and reception portion 42a receives a response signal from the slave device (here, the measurement device 10 as one example) in reply to the beacon signal (YES in S42), the measurement device determination portion 41a records, as communication information in the memory portion 5a, information of the slave device contained in the response signal together with other information necessary for communication (S43), thereby allowing communication with the slave device. In other words, pairing is established. Here, examples of the communication information include identification information of the slave device, key information for encryption communication, etc.

The external device 14 receives confirmation information from the paired slave device (S44). The confirmation information may be contained in a header of data transmitted from the measurement device 10, for example. The measurement device determination portion 41a receives the input of confirmation information from a user (S45). The measurement device determination portion 41a compares the confirmation information received from the slave device in S44 with the confirmation information received from the user in S45 (S46), and causes the transmission and reception portion 42a to transmit a deletion command to the slave device when they do not match each other (S47). Further, the measurement device determination portion 41a deletes the communication information recorded in S43 (S48). Thereby, the pairing can be cancelled both in the external device 14 and the slave device.

Incidentally, also when there is no input after a certain period of time from the start of reception of input of confirmation information in S46, the measurement device determination portion 41a judges that erroneous pairing is established, and can cause the transmission and reception portion 42a to transmit a deletion command (S47). Further, when the confirmation information matches each other (YES) as a result of the comparison in S46, the measurement device determination portion 41a judges that processing of the data transmitted in association with confirmation information is possible, and may proceed to processing of said data in the external device 14. Thereby, based on the confirmation information transmitted from the paired slave device, the measurement device determination portion 41a can judge the usability of data transmitted from the slave device in the external device 14.

The operation of the measurement device 10 and the operation of the external device 14 are not limited to the above-described example. For example, the confirmation information transmitted from the measurement device 10 can be information input from a user in the measurement device 10. In this case, for example, by a user simply inputting certain information both in the measurement device 10 and the external device 14 that is communicable with the measurement device 10, it is possible to prevent establishment of communication between erroneous devices.

It also is possible to adjust the timing of transmitting confirmation information from the measurement device 10 to the external device 14 so that the confirmation information is transmitted at the time of pairing, not after completion of pairing. In this case, the measurement device 10 can decide at the time of pairing whether or not communication with an intended external device becomes possible. Further, the confirmation information may be transmitted together with data as in the above-described example, or may be transmitted alone separately from data.

As a modification example of the processing of judging the usability of data in the external device 14 using confirmation information, the external device 14 can display the confirmation information transmitted from the measurement device 10, and receive input whether or not the displayed confirmation information is information of the measurement device 10 intended by the user. In this case, since the user only needs to input YES or NO, the user's operation with respect to the external device 14 can be facilitated further.

As cancellation processing of a communication setting when the established communication (pairing) between the measurement device 10 and the external device 14 is judged as an erroneous communication, for example, data transmitted from the measurement device 10 can be set so as not to be used by an application of the external device 14, instead of deleting the communication information as in the above-described example. In this case, the external device 14 can request a user to input or confirm confirmation information again if data is transmitted from the erroneously paired measurement device 10.

As described above, in the present embodiment, the communication between the measurement device 10 and the external device 14 is established without the use of authentication information, and the measurement device 10 transmits confirmation information together with data to be transmitted to the external device 14 after establishment of communication. The confirmation information is information to control the usability of transmitted data in the external device 14. Hence, in the external device 14, it is possible to judge the legitimacy of data from the measurement device 10 and execute appropriate processing based on the judgment results. In other words, the present embodiment can solve disadvantages due to simplification of the communication setting operation between the measurement device and the external device, by devising the control of information from the measurement device. Thereby, the risk of transmitting data from the measurement device 10 to an erroneous external device can be reduced, while simplifying the communication setting operation.

Embodiment 2

Figure 5:
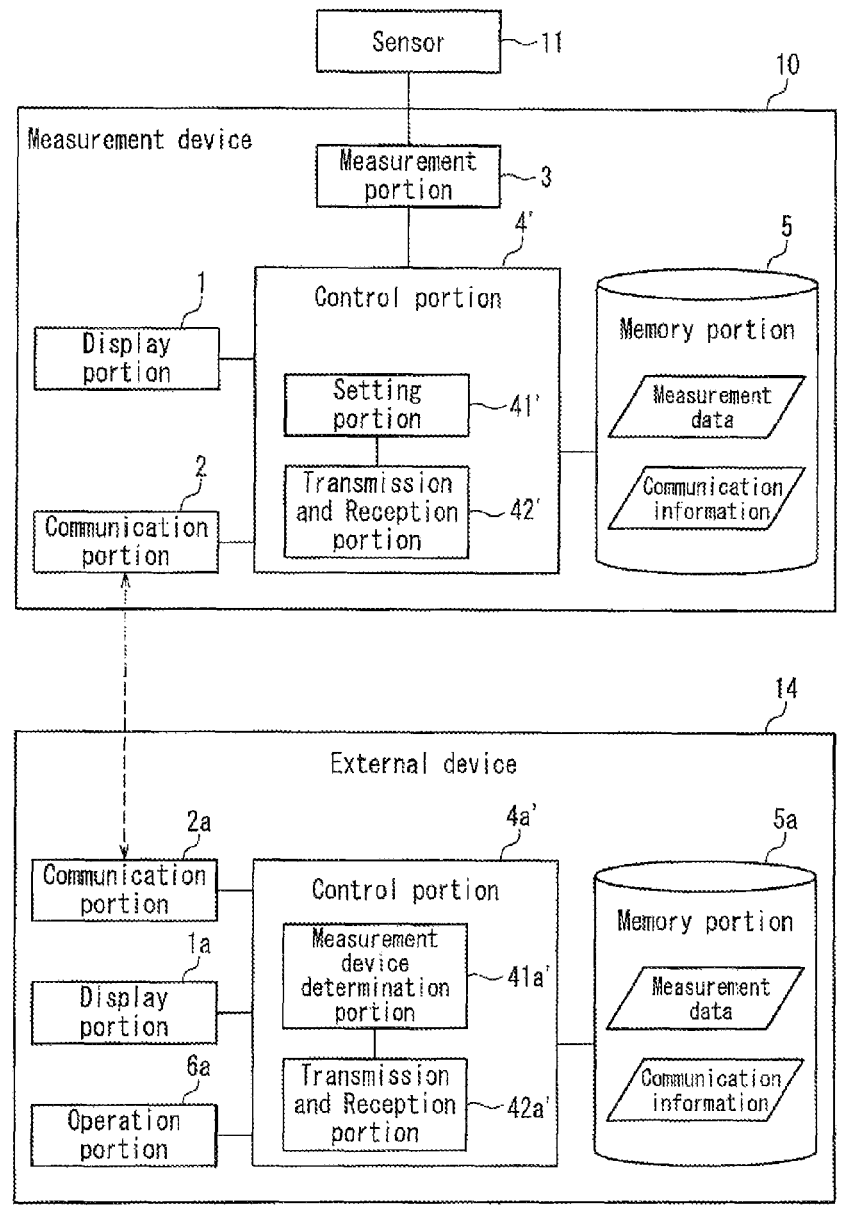
FIG. 5 is a functional block diagram showing an exemplary configuration of a measurement system according to Embodiment 2 of the present invention.

FIG. 5 is a functional block diagram showing an exemplary configuration of a measurement system according to Embodiment 2 of the present invention.

In the drawing, the present embodiment is mainly different from the above-described Embodiment 1 in that the above-described confirmation information is transmitted from the external device side to the measurement device side, and the measurement device executes comparison processing using the received confirmation information. The components common to those of the above-described Embodiment 1 are denoted with the same reference numerals and will not be described further.

As shown in FIG. 5, similarly to the measurement system of Embodiment 1, the measurement system of the present embodiment includes a measurement device 10 and an external device 14.

Exemplary Configuration of Measurement Device 10

In the example shown in FIG. 5, the measurement device 10 is provided with a display portion 1, a communication portion 2, a measurement portion 3, a control portion 4', and a memory portion 5. The measurement portion 3 acquires measurement data obtained by measurement. For example, the measurement portion 3 provides the control portion 4' with measurement values based on information obtained via a sensor 11. The control portion 4' includes a setting portion 41' and a transmission and reception portion 42'. The setting portion 41' specifies an external device as a transmission destination of measurement data based on a signal transmitted from the external device, and records information of the specified external device, thereby allowing communication with the external device. At this time, the setting portion 41' brings the measurement device 10 into a state communicable with the external device without receiving input of authentication information. The transmission and reception portion 42' includes a transmission portion that transmits measurement data to the external device specified by the setting portion 41'. Further, the transmission and reception portion 42' can receive signals from the external device and data such as the above-described confirmation information. Other than this explanation, the transmission portion and the reception portion may be independent from each other.

The setting portion 41' causes the transmission and reception portion 42' to transmit identification information of the measurement device for enabling mutual communication, with respect to the external device as a transmission source of the received signal. Further, the setting portion 41' decides whether or not the measurement data transmitted from the measurement device 10 can be handled based on confirmation information from the external device received by the transmission and reception portion 42'. Specifically, for example, the setting portion 41' decides whether or not the measurement data transmitted from the measurement device 10 can be handled, by comparing the confirmation information from the external device with confirmation information previously stored in the memory portion 5. Thereby, it is possible to establish communication between the external device 14 and the measurement device 10 with an easy operation, while avoiding erroneous establishment of communication.

In the above-described configuration, as in Embodiment 1, the measurement device 10 receives a signal from the external device, records information of the external device, and transmits identification information of the measurement device to the external device, thereby simplifying a user's operation when establishing communication with the external device. For example, the above-described configuration allows bidirectional communication without reception of authentication information from a user both in the external device and the measurement device. Further, unlike Embodiment 1, the measurement device 10 receives confirmation information from the external device at or after the establishment of communication with the external device as a transmission destination of measurement data. Thus, the measurement device 10 can decide using the confirmation information whether or not erroneous communication is set between the external device and the measurement device 10. In other words, the transmission of confirmation information from the external device to the measurement device 10 makes it possible to detect erroneous, not-intended communication setting.

The setting portion 41' can cause the display portion 1 of the measurement device 10 to display the confirmation information previously stored in the memory portion 5, thereby allowing a user to know the confirmation information of the measurement device 10. Further, the setting portion 41' also can cause the display portion 1 to display the confirmation information transmitted from the external device. Thus, it is possible to confirm that the communication established between the external device and the measurement device 10 is communication intended by the user. In this case, the setting portion 41' can cause the display portion 1 to display confirmation information at the timing of receiving the confirmation information.

The setting portion 41' can cancel the state communicable with the external device when judging the measurement data as not handleable based on the confirmation information transmitted from the external device. Thereby, it is possible to cancel the erroneously established communication setting with the external device. For example, the setting portion 41' of the measurement device 10 can judge whether the confirmation information transmitted from the external device matches the confirmation information previously held in the memory portion 5, and cause the transmission and reception portion 42' to notify the external device of the result. Further, when judging that they do not match each other, the setting portion 41' can cancel the state communicable with the external device. Examples of the cancellation processing include processing in the measurement device 10 of deleting information of the external device registered as a transmission destination of measurement data, and the like.

Exemplary Configuration of External Device 14

In the example shown in FIG. 5, the external device 14 is provided with a communication portion 2a, a display portion 1a, an operation portion 6a, a control portion 4a', and a memory portion 5a. The control portion 4a' includes a measurement device determination portion 41a' and a transmission and reception portion 42a'. The measurement device determination portion 41a' specifies a measurement device as a transmission source of measurement data based on a signal from the measurement device, and allows communication with the measurement device. The transmission and reception portion 42a' includes a reception portion that receives measurement data from the measurement device specified by the measurement device determination portion 41a'. Further, the transmission and reception portion 42a' can transmit signals, the above-described confirmation information, and the like to the measurement device. Other than this explanation, the transmission portion and the reception portion may be independent from each other.

The measurement device determination portion 41a' determines a measurement device for handling measurement data, based on confirmation information input by a user. Further, the measurement device determination portion 41a' transmits confirmation information of the determined measurement device to said measurement device via the transmission and reception portion 42a'. Other than this explanation, for example, when a plurality of measurement devices are in a state communicable with the external device, the measurement device determination portion 41a' may cause the display portion 1a to display confirmation information of those measurement devices, determine, as a measurement device for handling measurement data, a measurement device that has been selected by a user from among the confirmation information of those measurement devices, and cause the transmission and reception portion 42a' to transmit the confirmation information of the determined measurement device to said determined measurement device.

Further, when the external device 14 receives a notification from the measurement device that two sets of confirmation information do not match each other, i.e., when the external device 14 receives a signal (command) for canceling the state communicable with the measurement device via the transmission and reception portion 42a', the measurement device determination portion 41a' can cancel the state communicable with the measurement device. Examples of the cancellation processing include processing in the external device 14 of deleting information of the measurement device registered as a transmission source of measurement data, and the like.

The measurement device 10 can be composed of one computer, or a plurality of computers. The setting portion 41' and the transmission and reception portion 42' of the control portion 4' can be realized by execution of a predetermined program by a processor provided in the computer. For example, a microcontroller can be incorporated in the measurement device 10. As one example, such a microcontroller can include a core processor that constitutes the measurement portion 3, which generates measurement data by subjecting voltage signals transmitted from the sensor 11 to the AD conversion, and the control portion 4'.

The external device 14 also can be composed of one computer, or a plurality of computers. The measurement device determination portion 41a' and the transmission and reception portion 42a' of the control portion 4a' can be realized by execution of a predetermined program by a processor provided in the computer.

The following also are included as an embodiment of the present invention: a program for causing a computer to function as the setting portion 41' and the transmission and reception portion (transmission portion) 42', or a program for causing a computer to function as the measurement device determination portion 41a' and the transmission and reception portion (reception portion) 42a', and a non-transitory recording medium that records these programs. Moreover, a method for a computer to execute these programs is also included as an embodiment of the present invention.

For example, the following program is also one embodiment of the present invention:

a program for activating a computer as a measurement device, the program causing the computer to execute:

processing of acquiring measurement data obtained by measurement;

setting processing of specifying an external device as a transmission destination of the measurement data based on a signal transmitted from the external device, and recording information of the specified external device, thereby allowing communication with the external device without receiving input of authentication information; and transmission processing of transmitting the measurement data to the external device specified by the setting processing, wherein the setting processing includes:

transmitting identification information of the measurement device for enabling mutual communication with respect to the external device as a transmission source of the received signal;

receiving confirmation information that is used for decision of whether or not the measurement data transmitted from the measurement device can be handled; and deciding whether or not the measurement data transmitted from the measurement device can be handled based on the confirmation information.

Further, the following program also is one embodiment of the present invention:

a program for activating a computer that receives measurement data from a measurement device and processes the data, the program causing the computer to execute:

measurement device determination processing of specifying a measurement device as a transmission source of the measurement data based on a signal from the measurement device, and allowing communication with the measurement device without receiving input of authentication information; and reception processing of receiving the measurement data from the specified measurement device, wherein the measurement device determination processing of the external device includes:
receiving identification information of the measurement device from the measurement device;
receiving, at or after the reception of the identification information, input of confirmation information that is used for a decision of whether or not the measurement data transmitted from the measurement device can be handed; and
transmitting the confirmation information to the measurement device.

Exemplary Operation

Figure 6:
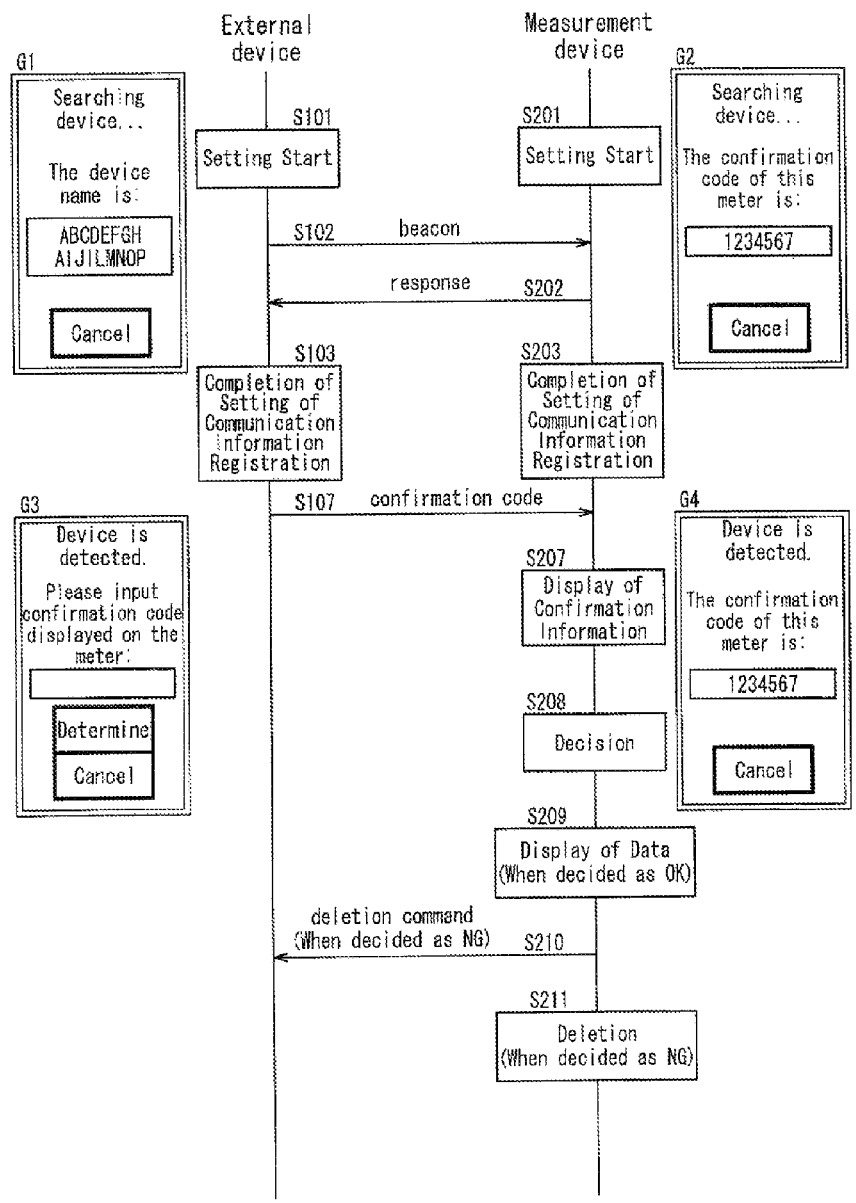
FIG. 6 is a sequence diagram showing an exemplary operation and an exemplary screen at the time of establishment of communication between a measurement device and an external device shown in FIG. 5.

FIG. 6 is a sequence diagram showing an exemplary operation and an exemplary screen at the time of establishment of communication between the measurement device 10 and the external device 14 shown in FIG. 5. As in the example shown in FIG. 2, the example shown in FIG. 6 is a case where the measurement device 10 and the external device 14 are paired in wireless communication based on Bluetooth (registered trademark) standards, thereby being communicable with each other. Further, in this embodiment, the operation proceeds in the same manner as in Embodiment 1 shown in FIG. 2 until the completion of pairing between the measurement device 10 and the external device 14, i.e., in the measurement device 10, from setting start S201 to completion of setting of communication information registration S203, and in the external device 14, from setting start S101 to completion of setting of communication information registration S103.

Upon completion of pairing, the external device 14 receives input of a confirmation code (exemplary confirmation information) from a user (exemplary screen G3), and transmits the input confirmation code to the measurement device 10 (S107).

The measurement device 10 causes the display portion 1 to display the received confirmation code (S207, exemplary screen G4). Then, in decision processing S208, the measurement device 10 compares the confirmation code transmitted from the external device 14 with a confirmation code previously stored in the memory portion 5. When they match each other, the measurement device 10 can execute processing of data transmitted from said measurement device 10. For example, processing of data (e.g., display of data (S209) etc.) transmitted from the measurement device 10 can be permitted.

Other than the above-described explanation, when the above-described two confirmation codes match each other in the decision processing S208, the measurement device 10 may notify the external device 14 of the match, thereby permitting the external device 14 to execute processing of data such as display of data transmitted from the measurement device 10, or causing both of the measurement device 10 and the external device 14 to execute processing of data such as display of the above-described data.

When the confirmation code previously stored in the memory portion 5 does not match the confirmation code transmitted from the external device 14 (confirmation information input by a user), both the external device 14 and the measurement device 10 execute processing of invalidating the paired device. For example, the measurement device 10 transmits a deletion command to the external device 14 (S210). By deleting the communication information recorded in the memory portion 5, the measurement device 10 can invalidate the communication setting between the external device 14 and the measurement device 10 (S211).

Thereby, even when erroneous pairing is established, it is possible to prevent exchange of data, leakage of personal information, etc.

Other than this explanation, the external device 14 may transmit a deletion command to the measurement device 10 (as will be described in detail later).

Figure 7:
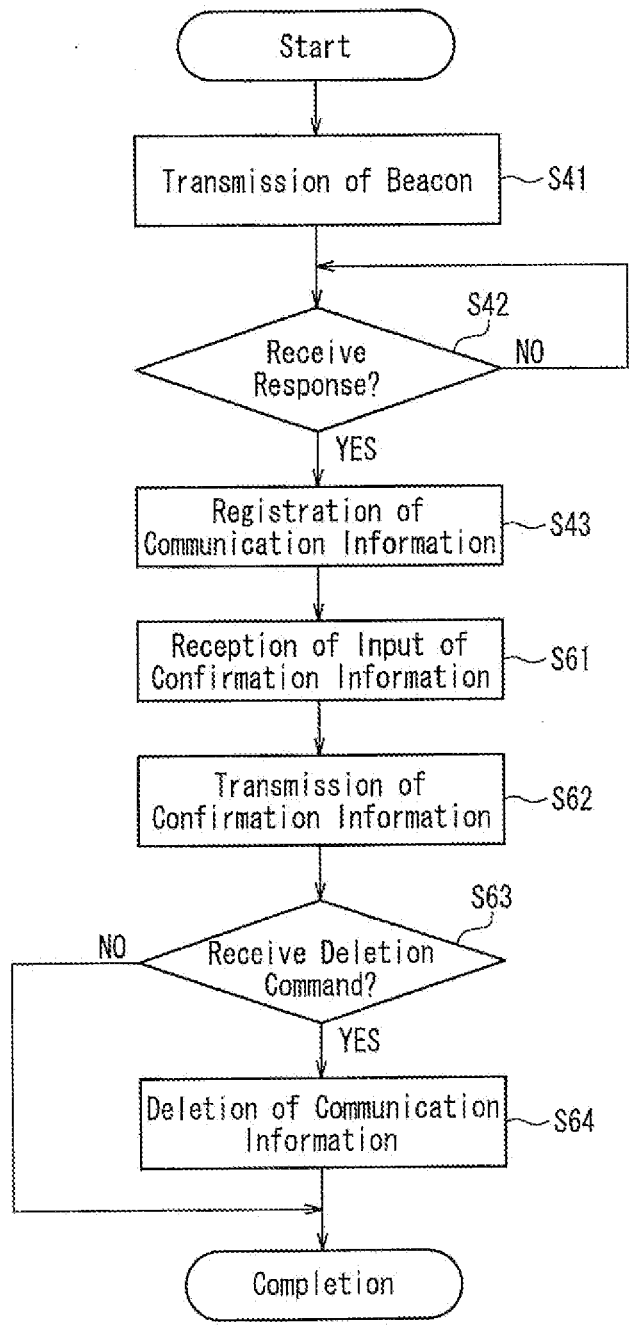
FIG. 7 is a flowchart showing exemplary setting processing by a measurement device determination portion of the external device shown in FIG. 5.

FIG. 7 is a flowchart showing exemplary setting processing by the measurement device determination portion 41a' of the external device 14 shown in FIG. 5. The example shown in FIG. 7 shows exemplary processing of the external device 14 in the communication setting processing shown in FIG. 6. When the external device 14 is switched to a communication setting mode (e.g., pairing mode), the measurement device determination portion 41a' causes the transmission and reception portion 42a' to transmit a beacon signal to search a peripheral slave device (S41).

When the transmission and reception portion 42a' receives a response signal from the slave device (here, the measurement device 10 as one example) in reply to the beacon signal (YES in S42), the measurement device determination portion 41a' records, in the memory portion 5a as communication information, information of the slave device contained in the response signal together with other information necessary for communication (S43), thereby allowing communication with the slave device. In other words, pairing is established. Here, examples of the communication information include identification information of the slave device, key information for encryption communication, etc.

In the external device 14, the measurement device determination portion 41a' receives input of a confirmation code from a user (S61). Then, for example, the measurement device determination portion 41a' transmits the input confirmation code to the paired measurement device 10 (slave device) via the transmission and reception portion 42a' (S62).

When the transmission and reception portion 42a' receives a deletion command from the slave device in reply to the confirmation information (YES in S63), the measurement device determination portion 41a' judges that pairing is established with an erroneous slave device, and deletes the communication information recorded in S43 (S64), thereby canceling the pairing with the slave device.

Other than this explanation, also when there is no input after a certain period of time from the start of reception of input of confirmation information in S61, the measurement device determination portion 41a' of the external device 14 judges that erroneous pairing is established, and can cause the transmission and reception portion 42a' to transmit a deletion command to the measurement device 10. Thus, both the external device 14 and the measurement device 10 execute processing of invalidating the paired device.

Figure 8:
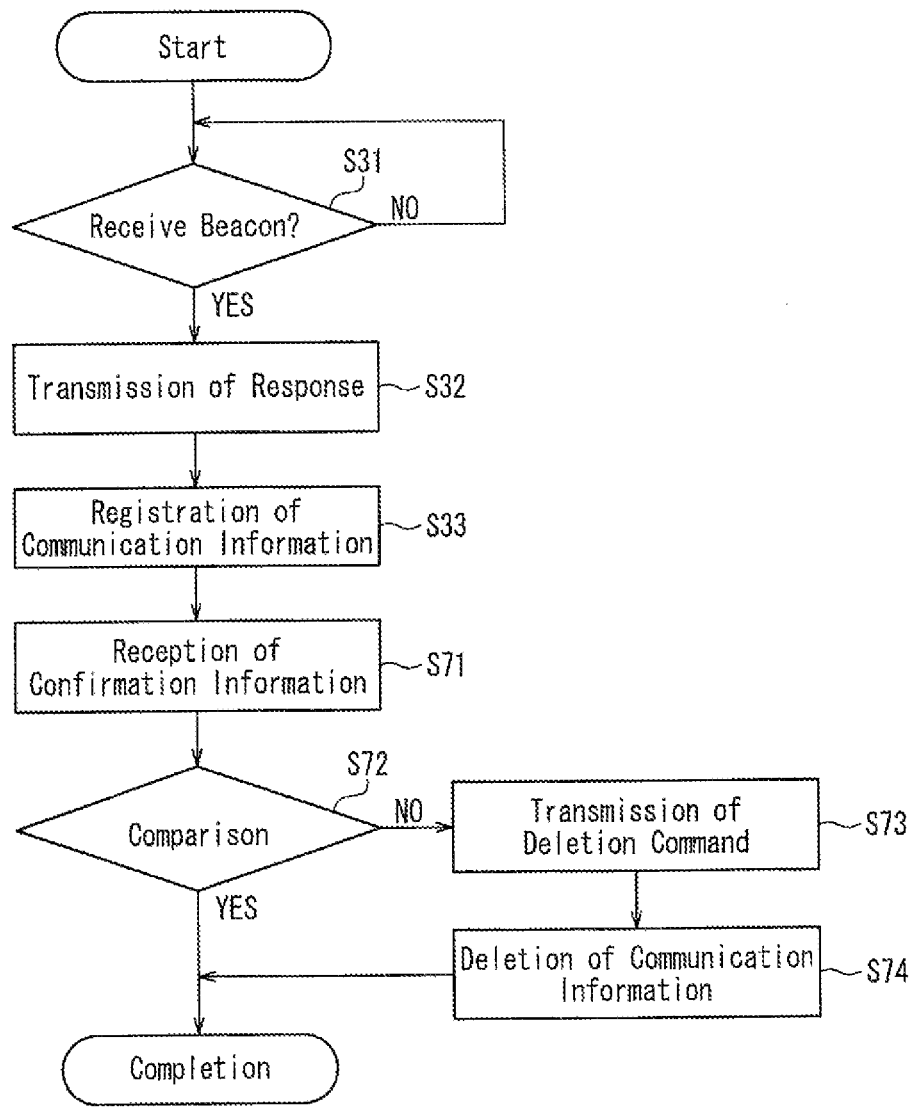
FIG. 8 is a flowchart showing exemplary setting processing by a setting portion of the measurement device shown in FIG. 5.

FIG. 8 is a flowchart showing exemplary setting processing by the setting portion 41' of the measurement device 10 shown in FIG. 5. The example shown in FIG. 8 shows exemplary processing of the measurement device 10 in the communication setting processing shown in FIG. 6. When the measurement device 10 is switched to a communication setting mode (e.g., pairing mode), the setting portion 41' waits for a beacon signal from a master device (S31). When the transmission and reception portion 42' receives a beacon signal, the setting portion 41' causes the transmission and reception portion 42' to transmit a response signal to the master device (here, the external device 14 as one example) as a transmission source of the beacon signal (S32). The response signal can contain identification information of the measurement device 10.

Upon completion of the transmission of the response signal, the setting portion 41' records, in the memory portion 5, information about the master device contained in the beacon signal received in S31 (S33), thereby allowing communication with the master device. In other words, pairing is established. In S33, communication information to be used for communication with the master device is recorded. Examples of the communication information include identification information of the master device, key information for encryption communication, etc.

The setting portion 41' causes the transmission and reception portion 42' to receive the confirmation information from the master device (S71). The setting portion 41' compares the confirmation information transmitted from the master device in S71 with the confirmation information previously stored in the memory portion 5 (S72), and causes the transmission and reception portion 42' to transmit a deletion command to the master device when they do not match each other (S73). Further, the setting portion 41' deletes the communication information recorded in S33 (S74). Thereby, the pairing can be cancelled both in the measurement device 10 and the master device.

Incidentally, when the sets of confirmation information match each other (YES) as a result of the comparison in S72, the setting portion 41' judges that processing of the data transmitted to the master device is possible, and may cause the display portion 1 to display said data. Further, the setting portion 41' may proceed to processing of said data in the external device 14. Thereby, based on the confirmation information transmitted from the paired master device, the slave device can judge the usability of data transmitted from the slave device in the external device 14.

Further, it is also possible to adjust the timing of transmitting confirmation information from the external device 14 to the measurement device 10 so that the confirmation information is transmitted at the time of pairing, not after completion of pairing. In this case, the measurement device 10 can decide at the time of pairing whether or not communication with an intended external device becomes possible.

As described above, in the present embodiment, the communication between the measurement device 10 and the external device 14 is established without the use of authentication information, and the external device 14 transmits confirmation information to the measurement device 10 after establishment of communication. The confirmation information is information to control the usability of transmitted data in the external device 14. Hence, in the external device 14, it is possible to judge the legitimacy of data from the measurement device 10 based on the presence or absence of the above-described deletion command and further to execute appropriate processing based on the judgment results. In other words, the present embodiment can solve disadvantages due to simplification of the communication setting operation between the measurement device and the external device, by devising the control of information from the measurement device. Thereby, the risk of transmitting data from the measurement device 10 to an erroneous external device can be reduced, while simplifying the communication setting operation.

Incidentally, other than the above-described explanation, instead of, or in addition to the configuration in which the measurement device 10 transmits the deletion command, when the sets of confirmation information match each other (YES) as a result of the comparison S72 in FIG. 8, the setting portion 41' may cause the transmission and reception portion 42' to transmit a permission command to the external device 14 for permitting the use of measurement data transmitted by the measurement device 10.

Exemplary Application to Blood Glucose Meter

The following describes a case of applying the present invention including the above-described Embodiment 1 or 2 to a measurement system of a blood glucose meter.

Figure 9:
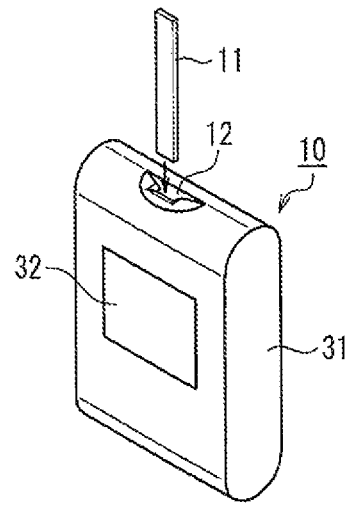
FIG. 9 is a perspective view showing an exemplary blood glucose meter that can be adopted as the measurement device.

FIG. 9 is a perspective view showing an exemplary blood glucose meter that can be adopted as the measurement device 10. Although in the example shown in FIG. 9, the measurement device 10 is a blood glucose meter, the present invention can be applied also to medical devices for measuring conditions of a living body, such as a sphygmomanometer, a lactic acid meter, a ketone body measurement device, a thermometer, a urine test paper meter, a lipid measurement device, and a pedometer. A main body 31 of the measurement device 10 houses an analysis device and a detector corresponding to the intended use. Further, the measurement device 10 is formed in a palm size, and can be carried by a user, such as a patient, a doctor, a nurse, etc.

As one example, the measurement device 10 can be a portable blood glucose meter that measures blood glucose levels of a patient. In this case, blood of a patient is provided to a sensor 11, and the main body 31 includes a sensor insertion slot 12 for insertion of a strip sensor 11. The sensor 11 has a reagent in its interior, and blood reacts with the reagent inside the sensor 11 beforehand. The main body 31 includes the communication portion 2, the measurement portion 3, the control portion 4 (or the control portion 4'), and the memory portion 5 described above. A display screen 32 is one example of the display portion 1. The measurement portion 3 inside the main body 31 has a function of measuring a glucose level from the blood reacted with the reagent by a colorimetric method or an electrochemical method. The measurement by the measurement device 10 starts immediately when the sensor 11 is inserted in the sensor insertion slot 12. The measurement results are recorded in the memory portion 5. The measurement results such as a record including glucose levels and measurement times can be recorded in a file in chronological order. Further, the measurement results are displayed on the display screen 32 of the main body 31. Such a blood glucose meter can be used as an SMBG (Self Monitoring of Blood Glucose) meter, for example.

Figure 10:
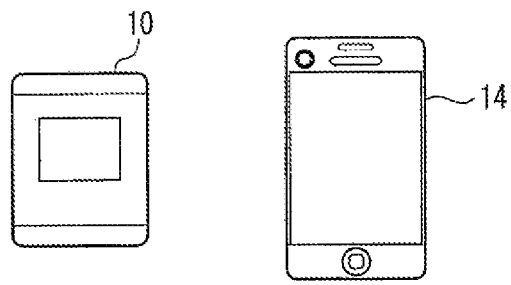
FIG. 10 shows the measurement device and the external device as one example.
Figure 11:
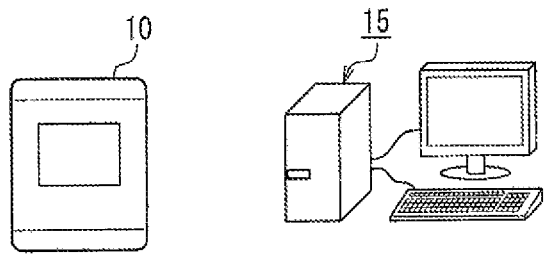
FIG. 11 shows the measurement device and the external device as another example.

For example, as shown in FIG. 10, the measurement device 10 can be communicable with a portable device 14, which is an exemplary external device. The portable device 14 can be a smartphone or a tablet terminal with a built-in computer, for example. Thus, data communication between the measurement device 10 and the portable device 14 becomes possible. Further, as shown in FIG. 11, the measurement device 10 and a general-purpose computer 15 (e.g., PC) can be communicable with each other. Examples of the external devices other than the above include a PDA, a portable game machine, and the like, although the applicable external devices are not limited to these examples.

As described above, by applying the measurement device of the above-described Embodiment 1 or 2 to a medical device such as a blood glucose meter, it is possible to solve problems particular to medical devices. For example, users of portable self-monitoring devices such as the above-described SMBG meter tend to be elderly people, and they often have difficulties in setting wireless communication with external devices by themselves. Hence, simplifying the setting operation is preferred. Further, it is assumed that explanatory meetings may be held or a plurality of measurement devices may be set simultaneously in medical institutions. In that case, a plurality of measurement devices respectively perform communication setting with a plurality of external devices simultaneously in the same place. In this situation, there is a high possibility that erroneous communication is set between a measurement device of a certain user and an external device of another user. There also is a high possibility that, since people who use a blood glucose meter may go to medical institutions at the same time, or have a chance to gather for diabetes camp, the external device and the measurement device under erroneous communication setting may meet again. If the communication setting is made erroneously, the measurement results obtained in another person's measurement device may be transmitted to his/her own external device. In that case, the data processing is executed based on another person's measurement results. Further, his/her own measurement results, which should be treated as personal information, may be displayed on another person's external device.

By the use of the measurement device of the above-described Embodiment 1 or 2, problems occurring due to such particular circumstances can be solved. According to the present embodiment, the communication setting is improved, i.e, facilitated. For example, pairing can be established using Bluetooth (registered trademark) version 4.0 without confirmation or input of a device name or a password both in the master device and the slave device. In this case, if two pairs of devices perform a pairing operation at the same timing within an area where radio waves reach, erroneous pairing may be established due to crossing. However, according to the above-described embodiment, confirmation information is transmitted from a measurement device as a slave device, and a master device can judge the appropriateness of the pairing using the confirmation information. Because of this, the data transmitted from the erroneously paired measurement device can be controlled so that the external device cannot use the data even if it receives the data. As a result, even when erroneous pairing is established, it is possible to prevent exchange of data and leakage of personal information.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A medical measurement device that acquires information about a subject body, comprising:
   a measurement portion that acquires measurement data obtained by measurement;
   a memory portion;
   a setting portion that specifies an external device as a transmission destination of the measurement data based on a signal transmitted from the external device, and records information of the specified external device in the memory portion to complete pairing between the medical measurement device and the specified external device, thereby allowing communication in a pairing mode with the external device without receiving input of authentication information; and
   a transmission and reception portion that transmits the measurement data to the external device specified by the setting portion and receives data from the external device,
   the setting portion causing the transmission and reception portion to transmit identification information of the measurement device for enabling mutual communication with respect to the specified external device, and after the pairing mode is established between the measurement device and the specified external device, further to transmit or receive confirmation information that is used for a decision of whether or not the measurement data transmitted from the measurement device is to be handled between the measurement device and the external device,
   the confirmation information including information which enables the specified external device to handle the measurement data transmitted from the measuring device by comparing input received from a user of the specified external device with the confirmation information.

2. The measurement device according to claim 1, wherein the setting portion causes the transmission and reception portion to transmit the confirmation information to the external device in addition to the identification information at or after the transmission of the identification information of the measurement device.

3. The measurement device according to claim 2, wherein the setting portion specifies the external device as a transmission destination of the measurement data, and causes the transmission and reception portion to transmit the confirmation information to the external device after being communicable with the external device.

4. The measurement device according to claim 2, wherein the setting portion causes a display portion of the measurement device to display the confirmation information.

5. The measurement device according to claim 2,
   wherein the setting portion causes the transmission and reception portion to transmit the confirmation information to the external device in association with measurement data to be transmitted by the transmission and reception portion, and
   the confirmation information is information to be used by the external device to decide the usability of the measurement data in the external device.

6. The measurement device according to claim 2, wherein the setting portion cancels a state communicable with the external device when receiving a notification from the external device that the external device has judged the measurement data as not handleable based on the confirmation information.

7. The measurement device according to claim 1, wherein the setting portion decides whether or not measurement data transmitted from the measurement device is to be handled based on the confirmation information transmitted from the external device.

8. The measurement device according to claim 7, wherein the setting portion causes a display portion of the measurement device to display the confirmation information.

9. The measurement device according to claim 8, wherein the setting portion cancels a state communicable with the external device when judging the measurement data as not handleable based on the confirmation information.

10. A medical measurement system, comprising:
    a medical measurement device that acquires information about a subject body; and
    an external device,
    wherein the measurement device includes:
       a measurement portion that acquires measurement data obtained by measurement;
       a memory portion;
       a setting portion that specifies the external device as a transmission destination of the measurement data based on a signal transmitted from the external device, and records information of the specified external device in the memory portion to complete pairing between the medical measurement device and the specified external device, thereby allowing communication in a pairing mode with the external device without receiving input of authentication information; and a transmission and reception portion that transmits the measurement data to the external device specified by the setting portion and receives data from the external device, and the external device includes:

a measurement device determination portion that specifies a measurement device as a transmission source of the measurement data based on a signal from the measurement device, and allows communication with the measurement device without receiving input of authentication information; and a reception portion that receives the measurement data from the specified measurement device, the setting portion of the measurement device causing the transmission and reception portion to transmit identification information of the measurement device for enabling mutual communication with respect to the specified external device, and after the pairing mode is established between the measurement device and the specified external device, further to transmit or receive confirmation information that is used for a decision of whether or not the measurement data transmitted from the measurement device is to be handled between the measurement device and the external device, the confirmation information including information which enables the specified external device to handle the measurement data transmitted from the measuring device by comparing input received from a user of the specified external device with the confirmation information.

11. The measurement system according to claim 10, wherein the setting portion of the measurement device causes the transmission and reception portion to transmit the confirmation information with respect to the external device, and the measurement device determination portion of the external device decides whether or not the external device is to handle the measurement data transmitted from the measurement device based on the confirmation information transmitted from the measurement device.

12. The measurement system according to claim 10, wherein the setting portion of the measurement device causes the transmission and reception portion to receive the confirmation information from the external device, and the setting portion of the measurement device decides whether or not the measurement device is to handle the measurement data transmitted from the measurement device based on the confirmation information transmitted from the external device.

13. The measurement device according to claim 1, wherein when the input received from the user of the specified external device and the confirmation information do not match, the transmission and reception portion receives or transmits a deletion command from or to the specified external device and the setting portion deletes the information of the specified external device recorded in the memory portion.

14. The measurement system according to claim 10, wherein when the input received from the user of the specified external device and the confirmation information do not match, the transmission and reception portion receives or transmits a deletion command from or to the specified external device and the setting portion deletes the information of the specified external device recorded in the memory portion.

* * * * *